United States Patent [19]

Popoff et al.

[11] 4,299,918

[45] Nov. 10, 1981

[54] METHOD FOR MULTIPLE ANALYSES

[75] Inventors: Michel Popoff, Plaisir; Marie-José Brochon, Fontenay sous Bois; Georges Brault, Savigny sur Orge, all of France

[73] Assignee: Institut Pasteur, Paris, France

[21] Appl. No.: 166,104

[22] Filed: Jul. 7, 1980

Related U.S. Application Data

[62] Division of Ser. No. 922,340, Jul. 6, 1978, Pat. No. 4,237,096.

[30] Foreign Application Priority Data

Jul. 6, 1977 [FR] France ............................ 77 20846

[51] Int. Cl.[3] ............................................ C12Q 1/24

[52] U.S. Cl. ...................................... 435/30; 435/32; 435/33; 435/34

[58] Field of Search ........................ 422/61, 102, 103; 73/440; 137/262, 263, 883; 141/35, 113, 236, 244; 435/287, 292, 293, 294, 296, 317, 808, 810, 30, 32, 33, 34

[56] References Cited

U.S. PATENT DOCUMENTS

| | | | |
|---|---|---|---|
| 829,460 | 8/1906 | Bunce | 73/440 |
| 1,873,010 | 8/1932 | Mitton | 73/422 TC |
| 3,631,727 | 1/1972 | White | 73/440 |
| 4,237,096 | 12/1980 | Popoff et al. | 422/102 |

*Primary Examiner*—Robert J. Warden

*Attorney, Agent, or Firm*—Weiser, Stapler & Spivak

[57] ABSTRACT

The invention relates to a device and a method for carrying out simultaneously multiple analyses in a liquid medium. The device comprises a compartment for introducing liquid, communicating through a distribution channel with separate analysis compartments. Each analysis compartment is provided with valve-forming means, such as a ball, isolating the liquid contained in the analysis compartment from the liquid remaining in the distribution channel. The device is particularly suitable for microbiological analyses.

2 Claims, 3 Drawing Figures

METHOD FOR MULTIPLE ANALYSES

This is a divisional of application Ser. No. 922,340, filed July 6, 1978 now U.S. Pat. No. 4,237,096.

BACKGROUND OF THE INVENTION

The invention relates to a device for carrying out multiple analyses effected simultaneously in a liquid medium.

Laboratories, in particular those of biochemical or medical analysis, must face an increasing number of routine analyses. These analyses, although systematic, require practically the same precautions as an isolated operation. To avoid as far as possible the risk of error, it is hence obligatory to provide devices simplifying the necessary manipulations. At the same time, it is necessary to arrive at simplified operations requiring a minimum of know-how and lending themselves if necessary to automatized processing.

It is an object of the invention to provide a device responding at least in part to these requirements. It is aimed more particularly to analyses carried out in liquid media and for which the same sample is subjected to various reaction conditions (or developments when it relates to micro-organisms).

GENERAL DESCRIPTION OF THE INVENTION

The device according to the invention for the production of multiple analysis reactions in a liquid medium (non-solid) comprises: a supply or introduction compartment, a series of separate analyses compartments, the supply compartment communicating with each of the analysis compartments through a distribution channel, each analysis compartment being provided with valve-forming means to isolate the liquid contained in the analysis compartment from that which remains in the supply channel once the level of the liquid introduced into the device is stabilized.

Preferably, the various introduction and analysis compartments and the distribution channel are arranged with respect to one another, so that the liquid introduced is distributed by the simple effect of gravity in the various analysis compartments.

The valve-forming means may be formed in very varied ways according to traditional methods. Taking into account the use which is made of the devices according to the invention, and in particular that they are preferably of service no more than once, it is however preferable that these means be as simple as possible. Such a device is produced, for example, by arranging the orifice, through which the analysis compartment communicates with the distribution channel, in the lower portion of the compartment, and in placing in the compartment a movable solid element denser than the liquid medium used in the course of the analysis and which in resting position, that is to say, when the hydrostatic equilibrium is established in the device, closes the orifice by covering it.

In practice, it is advantageous, to form the valve by using a ball of inert material in combination with a circular communicating orifice, so that the ball, falling under the effect of its own weight, becomes positioned automatically on the orifice and ensures suitable closing of the latter. It is advantageous to form the bottom of the tube to facilitate the positioning of the ball. For example, it will have a conical or hemispherical shape centered on the orifice.

The invention is obviously not limited to the previously indicated embodiment. The valve-forming means isolating the analysis compartment and the seat of this means which corresponds to it in the compartment can assume very varied shapes. It is possible thus to use a valve in the form of a cylindrical, conic, disc or any other means serving the same purpose.

The shape or the size of the analysis or of the introduction compartments are not critical. For the analysis compartments, it is advantageous that the latter have the shape of tubes or cells customarily used in this field, which permits varied use in traditional measuring equipment, notably for spectrophotometric measurements. Parallelepipedic cells are particularly preferred.

The number of analysis compartments of the device is a function of the study to be carried out. The more numerous the compartments, the more numerous are the independent parameters of the same sample which can be determined in a single operation.

The introduction compartment may also take very varied shapes and sizes without the operation of the device being modified thereby. To enable the liquid introduced to flow from the supply compartment to the different analysis compartments, the former must be situated at the same level or at a higher level than the second. In a particularly simple preferred embodiment, the introduction compartment is identical with the analysis compartments with the slight difference that it communicates freely with the distribution channel, in other words that it is not separated from the latter by valve-forming means.

It may also be advantageous to limit the volume of the supply compartment to reduce the "dead" space of the liquid sample introduced into the device, that is to say the volume of liquid which is not used in the analysis proper. To this end, the supply compartment may be constituted by a single channel of which the opening is situated above the level which the liquid medium must reach in the analysis compartments. In this case, it is possible to provide a flaring of the compartment above this level to facilitate the introduction of the liquid, or again to adapt the shape of the opening of the filling compartment to the means by which the sample under analysis is introduced into this compartment. Such an arrangement is particularly advantageous when the device according to the invention is filled by means of an automatized sampling apparatus.

The analysis compartments of the series may be identical, but it is also possible to vary their characteristics. It is possible notably to provide analysis compartments of different volumes in the same device. To this end, the dimensions of the cross-section of the compartment can be varied. It is also possible, for constant cross-sections, to arrange that the bottom of the compartment is situated at different levels.

An important advantage of the device according to the invention is to permit the selection and measuring out of reactants systematically for given analyses. It is necessary for these reactants to be kept until use in the analysis compartment which is assigned to them. It is possible to introduce these reactants on the preparation of the device, in a measured amount (a function of the useful volume of this compartment). It is also possible to arrange several reactants in the same compartment on condition that they do not run the risk of causing, before use, reactions incompatible with the normal utilization in the proposed analysis. Taking into account the arrangement of the device, it is advantageous to arrange that the reactants are retained in each compartment and cannot accidentally pass from one compartment to the distribution channel or, through the latter, to another compartment. To this end, it is of course desirable to use reactants in a physical form which permits their immobilization. It can be a compound of high viscosity adhering to the inner wall of the compartment. The reactant may also be mixed with a viscous product inert with respect to the contemplated reaction and having the function of fixing the reactant mechanically until its use in the reaction medium. More frequently, it is possible to use reactants in the dry state. If the latter risk passing into the device, it is then advantageous to make them fast to a support which cannot pass through the orifice connecting the compartment with the rest of the device.

It is particularly advantageous to take as a support for the one or more reactants, the movable solid element forming the valve of the compartment. To facilitate the fixing of the reactants, one may use, to form this element, a more or less porous material. A particularly suitable fixing method consists of impregnating the element of porous material with a solution or suspension of the reactant, and then drying the whole. When several reactants must be introduced into the same compartment, it is possible to provide, in addition to the movable solid element serving as a valve and possibly as a reactant support, other reactant support elements. The latter may also take the form of porous balls impregnated by means of the reactants concerned whether in the dry state or not.

The distributing channel communicating the supply compartment and the analysis compartments may be a single or multiple channel; it can also be branched. In the preferred form, for which the different compartments are aligned, a single distributing channel suffices, with short branches opening into each analysis compartment. This arrangement has the advantage of limiting the amount of unnecessary liquid medium.

Materials useful for constructing the device according to the invention must essentially be inert with respect to the reactants or the products resulting from the reactions set up. For a large number of conventional analyses, it is necessary for the analysis compartments to lend themselves to visual observations or optical measurements. Consequently, it is preferable to use transparent materials. For analyses in which microorganisms take part, it is also necessary for the materials of the devices to be capable of supporting sterilization.

Advantageous materials are notably glass and synthetic plastics materials such as polyvinyls, polystyrene, polyesters, polyamides, polycarbonates such as those marketed under the names "Macrolon," "TPX" or "Trogamide." The latter are particularly suitable to the extent that they can facilitate the forming of the selected shapes by techniques of molding or thermoforming, and may, in addition, be welded or worked in any conventional manner. Their low cost ties in well with the principle of the devices designed for a single utilization.

DESCRIPTION OF A PREFERRED EMBODIMENT

In the remainder of the description, reference is made to an embodiment of the device according to the invention, given purely by way of illustrative but non-limiting example.

BRIEF DESCRIPTION OF THE DRAWINGS

This example is illustrated by the accompanying drawings in which.

DETAILED DESCRIPTION

Figure 1:
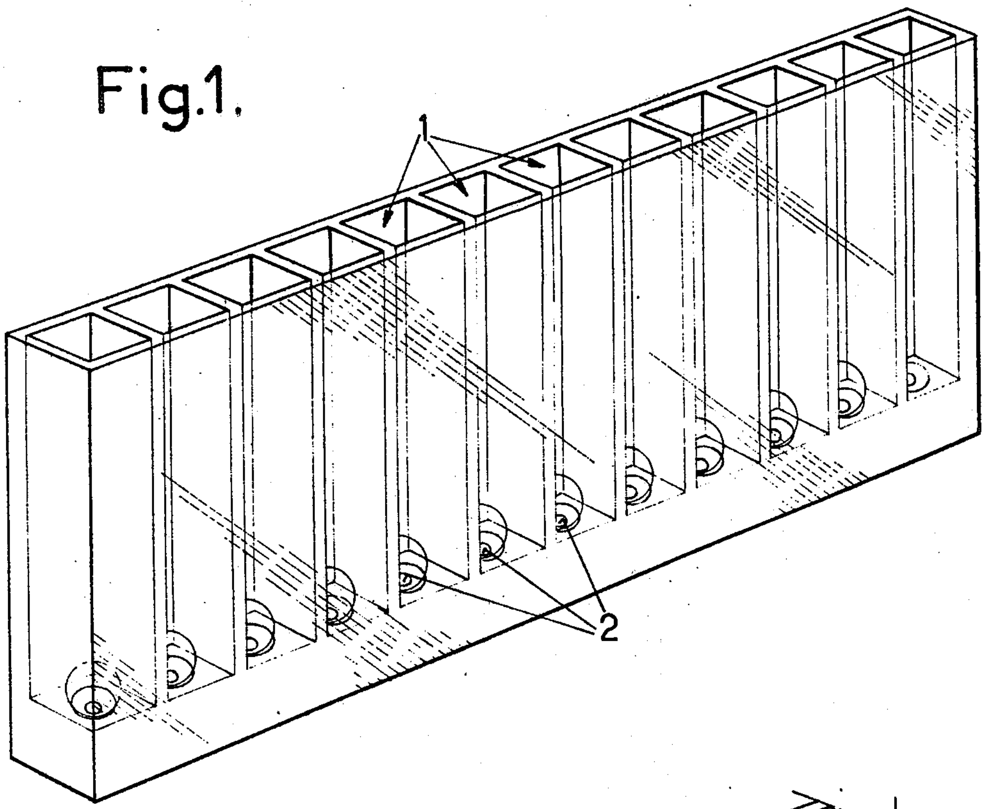
FIG. 1 shows a diagrammatic perspective view of an embodiment of the device according to the invention.
Figure 2:
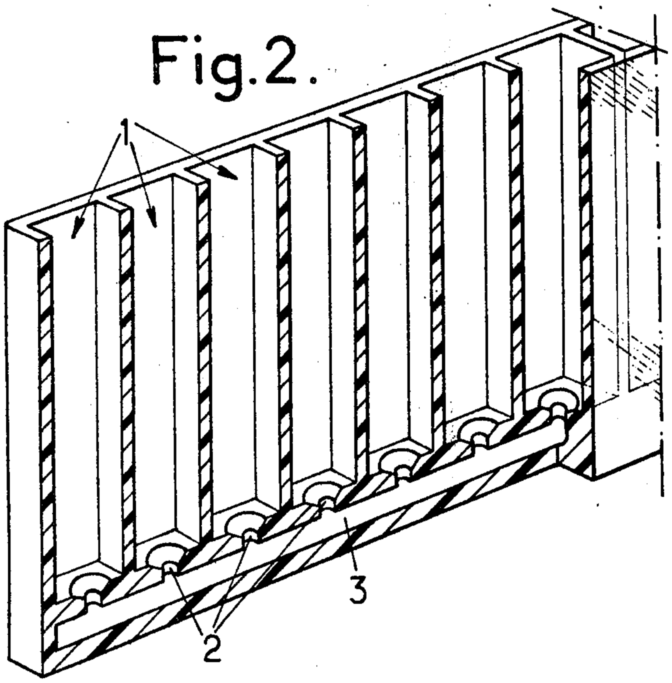
FIG. 2 shows, enlarged, a partial section of a portion of the device in which the valve forming ball is not shown.

In the embodiment of FIGS. 1 and 2, the device is in the form of a series of aligned compartments. Each compartment 1, of parallelepipedic shape, includes at its lower portion an orifice 2, formed by a cylindrical duct with a conical opening on the side of said compartment. The duct opens into a distributing channel 3. The balls, not shown, are of a diameter greater than that of the duct 2. The last compartment of the series does not contain a ball and is used as an introduction compartment.

In the figures, the various compartments are open over their whole cross-section at the upper portion. It is also possible to provide openings of smaller cross-section. It suffices, in fact, for utilization, for the analysis compartment to have an opening through which the gas contained in the compartment can escape freely to enable the liquid to enter the compartment without exerting pressure. The filling compartment must, for its part, have a sufficient opening to enable the introduction of the liquid analyzed through conventional means (burettes, pipettes, syringes, etc.).

Before use, in the embodiment illustrated, the upper opening of the compartment is closed by a thin breakable membrane. This membrane, not shown, has first the purpose of maintaining, in the device, the movable balls between the moment of the preparation of the device and that of its utilization. The membrane closing the compartment serves then for avoiding any introduction of compounds foreign to the system. In particular, when the device is used for cultures of micro-organisms, a sealed closure after sterilization is a guarantee against accidental contamination.

The operation of the device according to the invention shown in FIGS. 1 and 2 is as follows.

When, as in the case of the example, the compartments are sealed by a membrane, the latter is pulled off, or torn, or perforated. Liquid serving as the reaction medium, and containing the specimen to be analyzed, is introduced into the introduction compartment which does not contain a ball. It flows from this introduction compartment into the distributing channel 3 and from there, through the communicating ducts 2, enters the analysis compartments 1 by slightly lifting the balls which normally close the orifices of the ducts.

Figure 3:
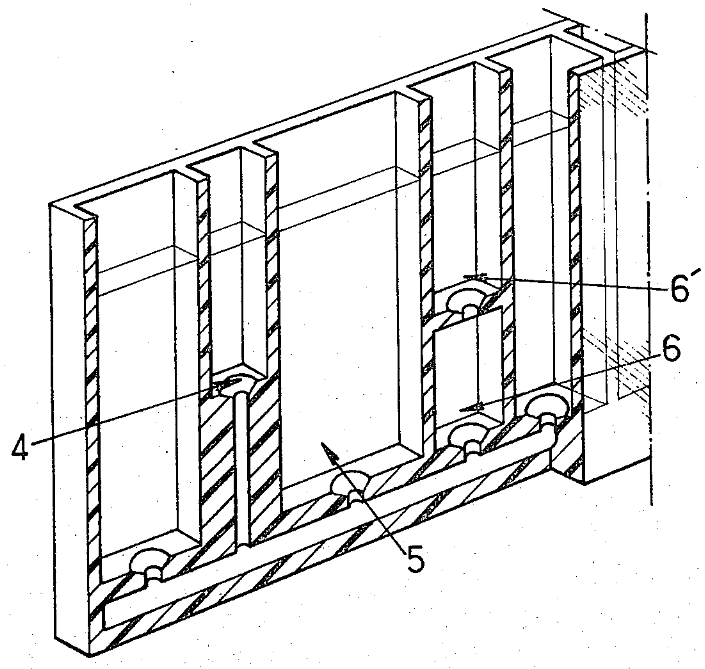
FIG. 3 shows a device according to the invention comprising several types of different compartments: one compartment 4 whose bottom is raised and cross-section diminished to reduce the useful volume, a compartment 5 of large cross-section, a compartment 6 and 6' forming two superposed portions each having a valve-forming system. (The level of the liquid is indicated by a thin line).

The operation of the device is the same whether the various compartments are identical, as shown in FIGS. 1 and 2, or whether they are different as in FIG. 3. When the level is stabilized in the various compartments, the ball falls back on the orifice, thus isolating each analysis compartment from the remainder of the device.

In practice, so that the device may operate under the best conditions, it is necessary to use balls whose density, although greater than that of the liquid, is not excessive, so that the thrust of the liquid, due to the difference in level between the supply compartment and in the various analysis compartments, suffices to displace the ball. It is also advantageous for the distributing channel to have a cross-section sufficiently greater than that of the communicating ducts 2 so that all the analysis compartments are filled at the same time, and to avoid the differences in level which can be accompanied by a partial return of the contents from an analysis compartment into the distributing channel. The specimen liquid is mixed with the reactants contained in the analysis compartment.

An advantageous construction to provide for rapid, homogeneous and simultaneous filling of all the analysis compartments consists, when the compartments are aligned, of placing, at the end of the series opposite that where the introduction compartment is situated, a compartment without a valve system. In an arrangement of this type, the liquid introduced rises rapidly in the latter compartment due to the fact that no valve interferes with its advance. It is established at the same level as in the introduction compartment, and enables more regular distribution in each compartment, whether or not the latter is situated close to the introduction compartment.

When the ball is impregnated with one or several reactants, the mixture of these reactants with the liquid medium is facilitated by the "washing" of the ball by the flow of liquid entering the analysis compartment and which necessarily passes in contact with the ball. The mixture of reactants, once produced, the reaction or culture develops conventionally.

The ball may, in addition, be impregnated with a product which, in dissolving, increases the viscosity of the liquid. The modification of the medium thus achieved may be desired for its influence on the development of the analysis, but, in addition, th closing of the orifice 2 by the ball is all the better as the viscosity of the medium is greater.

It is remarkable to observe experimentally that by the device according to the invention, whose application is particularly simple, the partitioning of the various compartments is achieved very satisfactorily. It is observed thus that the diffusion of chemical products dissolved in one compartment to the other is practically zero under normal conditions of use. It is possible, under these conditions, to use the device according to the invention both for instantaneous reactions and for those which require several hours or even several days for their development to be complete. This is particularly advantageous and enables the use of this device for relatively long analyses such as those producing a culture of micro-organisms.

In practice, this system of closure by means of a ball is sufficient to prevent the passage of dissolved reactants from one compartment to another; on the other hand, it does not prevent the passage of micro-organisms which spread out through the whole of the device through the effect of their development or their own mobility.

This feature may be exploited to introduce separately into the device, on the one hand, the liquid medium, and, on the other hand, an inoculum of the micro-organism under study. This introduction in two stages may have certain advantages. Thus, the introduction of the liquid medium in a first stage permits, by the solution of the reactants, the establishment in each compartment of a perfectly homogeneous medium before the micro-organisms are placed in contact with this medium. It is moreover, easy to introduce a large volume of sterile liquid medium into the device, and this, if necessary, automatically, whilst the inoculum studied is normally in a small volume. By introducing the inoculum after the liquid medium, it is hence important for the micro-organisms to be able to spread out suitably into each analysis compartment. In the latter case, in addition to the inoculation of the compartments due to the progressive development of the culture or of the mobility of the micro-organism, it may be advantageous to arrange that the volume of inoculum introduced is sufficient for a fraction of this inoculum to enter directly into each compartment. This can be achieved by adjusting the volume of the inoculum so that is greater than the "dead" volume of the device. It is possible, for example, to use a volume of inoculum double of the dead spaces which comprise: the introduction chamber, the supply channel and the ducts opening into each analysis compartment. As has already been specified, this "dead" space may be limited to the strict minimum by reducing the cross-section of the channels, but especially by reducing the volume of the introduction compartment.

The operation of devices comprising two-stage compartments or if desired, two superposed compartments such as those shown in FIG. 3 (6 and 6'), enables the analysis carried out to be separated into two stages, thus it is possible by the double system of valves and reactants associated therewith, to carry out a first operation by filling the device so that only the lower compartment 6 is filled. In other words, the first introduction of liquid leads to a level located below the valve of the compartment 6'. A second admission of liquid leads the contents from the lower compartment 6 into the upper compartment 6' where a second operation can be carried out.

An example of the application of this device with superposed compartments is that of studying the behaviour of micro-organisms with respect to growth modifiers (an inhibitor or on the other hand, a growth factor). In this way, for example, the development of the micro-organism in the lower compartment 6 is effected by giving the medium a composition suitable for this development (and this notably by means of compounds which can be contained on the one or more balls present in this compartment). Once the development of the culture reaches the desired level, the addition of liquid medium brings a portion of the contents from this compartment 6 into the upper compartment 6' where it becomes contacted by this growth modifier. After the time necessary for the phenomena brought into play to be manifested, it is possible to compare the state of development of the cultures in each compartment and to deduce therefrom the proper role of the modifier used. Such a comparison may be carried out by any conventional means of analysis, whether it involves simple visual observation, measurement of optical density, or again any other measurement normally used for this type of determination (spectrometry, fluorescence, etc.).

The reaction medium containing the sample analyzed is necessarily liquid; nonetheless, a certain viscosity is not excluded. It is possible in particular to use so-called "viscous" culture media such as those which are the subject of French patent No. 75 23851, filed July 30, 1975, which media lend themselves indifferently to the culture of aerobic, anaerobic or aeroanaerobic micro-organisms. In all cases, the limiting viscosity is that for which the medium would no longer be sufficiently fluid to flow normally in the device. It is also possible to increase the cross-section of the various passages or ducts in the case where a particularly viscous liquid medium must be used.

Certain quantitative parameters of the reactions that are carried out may be fixed. In fact, it is first possible to measure out the reactants initially present in the analysis compartment, and it is also possible, the compartments of the device being calibrated, as was indicated above, for example, by acting on the cross-section or the level of the bottom of the compartment, to fix the volume isolated in each compartment by adjusting the total volume of liquid admitted into the device.

It is also possible, to avoid prior adjustment of the volumes introduced, to provide the device with an overflow opening, thereby fixing the level in the whole of the device.

The simplification and systematization of analyses by the utilization of the device according to the invention are particularly advantageous for automatizing operations, including possible measuring operations.

We claim:

1. In a device for use in carrying out simultaneously multiple analysis reactions in a liquid medium, said device comprising an introduction compartment adapted to receive the liquid, separate analysis compartments, a distributing channel communicating said introduction compartment with said analysis compartments, valve-forming means provided in each analysis compartment capable of isolating liquid contained in the analysis compartment from liquid remaining in the distribution channel, each valve-forming means being constituted by a movable solid element positioning itself in resting position so as to close the communication between the analysis compartment and the distribution channel, and opening this same communication under the effect of movement of the liquid on introduction of the liquid into the introduction compartment, the method of analysis comprising introducing in a single operation or successively through the valve-forming means, the liquid intended to form the culture medium with the possible constituents present in the analysis compartments, and the inoculum under study.

2. Method of analysis according to claim 1, wherein there is introduced into the introduction compartment, in a first operation, the liquid and the inoculum in such amount that only the lower portions of the analysis compartments are filled through the valve-forming means, and then after a sufficient time to enable the culture to be developed, in a second operation, there is introduced an additional amount of liquid into the introduction compartment which fills the upper portions of the analysis compartments through the valve-forming means, thus bringing into contact a fraction of the culture produced in the lower portions with the reactants contained in the upper portions.

* * * * *